(12) United States Patent
Oh et al.

(10) Patent No.: US 11,964,030 B2
(45) Date of Patent: *Apr. 23, 2024

(54) ROOT CANAL FILLER COMPOSITION AND METHOD FOR PREPARING SAME

(71) Applicant: VERICOM CO., LTD., Chuncheon-si (KR)

(72) Inventors: Myunghwan Oh, Seoul (KR); Dohyun Kim, Siheung-si (KR); Jongho Kang, Bucheon-si (KR); Jiyeon Suh, Seoul (KR); Yunki Kim, Anyang-si (KR)

(73) Assignee: VERICOM CO., LTD., Chuncheon-si (KR)

( * ) Notice: Subject to any disclaimer, the term of this patent is extended or adjusted under 35 U.S.C. 154(b) by 605 days.

This patent is subject to a terminal disclaimer.

(21) Appl. No.: 17/273,165

(22) PCT Filed: Aug. 1, 2019

(86) PCT No.: PCT/KR2019/009591
§ 371 (c)(1),
(2) Date: Mar. 3, 2021

(87) PCT Pub. No.: WO2020/050505
PCT Pub. Date: Mar. 12, 2020

(65) Prior Publication Data
US 2021/0338536 A1    Nov. 4, 2021

(30) Foreign Application Priority Data
Sep. 6, 2018   (KR) .................. 10-2018-0106492

(51) Int. Cl.
| | | |
|---|---|---|
| *A61K 6/54* | (2020.01) | |
| *A61K 6/838* | (2020.01) | |
| *A61K 6/853* | (2020.01) | |
| *A61K 6/86* | (2020.01) | |

(52) U.S. Cl.
CPC ................ *A61K 6/54* (2020.01); *A61K 6/838* (2020.01); *A61K 6/853* (2020.01); *A61K 6/86* (2020.01)

(58) Field of Classification Search
CPC . A61K 6/54; A61K 6/838; A61K 6/86; A61K 6/853
See application file for complete search history.

(56) References Cited

U.S. PATENT DOCUMENTS
2013/0023601 A1   1/2013   Ogliari et al.

FOREIGN PATENT DOCUMENTS

| JP | 2010518093 A | 5/2010 |
| KR | 1020090054302 A | 5/2009 |
| KR | 1020100037979 A | 4/2010 |
| KR | 1020150144028 A | 12/2015 |
| KR | 101956859 B1 | 3/2019 |
| WO | WO 2018/164436 | * 9/2018 |

OTHER PUBLICATIONS

International Search Report of PCT/KR2019/009591, dated Oct. 24, 2019, English translation.

* cited by examiner

*Primary Examiner* — C Melissa Koslow
(74) *Attorney, Agent, or Firm* — STIP Law Group, LLC

(57) ABSTRACT

The present disclosure provides a root-canal sealer composition including cement and a hygroscopic liquid, in which the cement includes tricalcium silicate ($3CaO \cdot SiO_2$) in which an aluminum atom (Al) is solid-soluted (Al solid-soluted C3S), dicalcium silicate ($2CaO \cdot SiO_2$) in which an aluminum atom (Al) is solid-soluted (Al solid-soluted C2S), and tricalcium aluminate ($3CaO \cdot Al_2O_3$) in which a silicon atom (Si) is solid-soluted (Si solid-soluted C3A), the tricalcium aluminate being disposed between at least one selected from the group consisting of the Al solid-soluted C3S and the Al solid-soluted C2S. When the cement including aluminum solid-soluted tricalcium silicate, aluminum solid-soluted dicalcium silicate, and silicon solid-soluted tricalcium aluminate is prepared and used for a root-canal sealer composition, a curing time is reduced and compressive strength is increased. Also, the root-canal sealer composition is effective at ensuring a sufficient working time, thereby improving workability and storage stability.

17 Claims, 8 Drawing Sheets

ROOT CANAL FILLER COMPOSITION AND METHOD FOR PREPARING SAME

CROSS-REFERENCE TO RELATED APPLICATIONS

This application is the U.S. National Phase under 35 U.S.C. § 371 of International Application No. PCT/KR2019/009591 filed on Aug. 1, 2019, which in turn claims the benefit of Korean Application No. 10-2018-0106492 filed on Sep. 6, 2018, the disclosures of which are incorporated by reference into the present application.

TECHNICAL FIELD

The present disclosure relates to a root-canal sealer composition and a method of preparing the same, and more particularly to a root-canal sealer composition including cement in which an aluminum atom or a silicon atom is solid-soluted and a hygroscopic liquid, and a method of preparing the same.

BACKGROUND ART

In the case in which a dental cavity has progressed to the pulp, which is the innermost portion of the tooth, root-canal treatment is performed in a manner in which the pulp is removed and the root canal is sealed with hydraulic cement. A root-canal sealer therefor comes into direct contact with biotissue and thus preferably has to exhibit high biocompatibility, high sealability and antibacterial activity to prevent infection due to residual bacteria, workability to completely fill the root canal with the cement, and high curability to prevent the sealer from being lost during hydrocuring in the root canal. Moreover, in the case in which the cement cured in the root canal cracks or fractures due to external stress, infection may be caused by poor sealability, so appropriate compressive strength thereof must be exhibited.

As a root-canal sealer material that satisfies biocompatibility, sealability, and antibacterial activity, MTA (mineral trioxide aggregate), containing calcium silicate cement and bismuth oxide, which is a radiopaque material, has been widely used. Calcium silicate cement in MTA forms a C-S-H gel (calcium-silicate-hydrate gel) during hydrocuring and exhibits high strength, during which calcium hydroxide is formed as a byproduct and an alkaline pH environment is created to impart antibacterial activity.

However, despite these advantages of MTA, there is a disadvantage of having a long curing time of 3 hours or more, and thus some of the sealer is likely to be washed away by body fluids in the oral cavity during the curing process. Thereby, bacterial infection may occur due to a decrease in the sealing effect, and the apparent density of the cured sealer decreases, so cracking may easily occur due to external stress, and there is a risk of infection.

Therefore, in order to solve the problems with the existing root-canal sealer composition, the development of a root-canal sealer composition having a sufficient working time and fast curing time and exhibiting high compressive strength is required.

DISCLOSURE

Technical Problem

An objective of the present disclosure is to provide a root-canal sealer composition having a reduced curing time and increased compressive strength by preparing cement including aluminum solid-soluted tricalcium silicate, aluminum solid-soluted dicalcium silicate, and silicon solid-soluted tricalcium aluminate.

Another objective of the present disclosure is to provide a root-canal sealer composition capable of ensuring a sufficient working time and having improved storage stability.

Technical Solution

An aspect of the present disclosure provides a root-canal sealer composition including cement and a hygroscopic liquid, in which the cement includes tricalcium silicate ($3CaO \cdot SiO_2$) in which an aluminum atom (Al) is solid-soluted (Al solid-soluted C3S), dicalcium silicate ($2CaO \cdot SiO_2$) in which an aluminum atom (Al) is solid-soluted (Al solid-soluted C2S), and tricalcium aluminate ($3CaO \cdot Al_2O_3$) in which a silicon atom (Si) is solid-soluted (Si solid-soluted C3A), the tricalcium aluminate being disposed between at least one selected from the group consisting of the tricalcium silicate in which the aluminum atom (Al) is solid-soluted (Al solid-soluted C3S) and the dicalcium silicate in which the aluminum atom (Al) is solid-soluted (Al solid-soluted C2S).

The tricalcium silicate in which the aluminum atom is solid-soluted may be obtained through substitution of a portion of a silicon atom of the tricalcium silicate with the aluminum atom, or through entry of the aluminum atom into interstices of a crystal lattice of the tricalcium silicate.

The dicalcium silicate in which the aluminum atom is solid-soluted may be obtained through substitution of a portion of a silicon atom of the dicalcium silicate with the aluminum atom, or through entry of the aluminum atom into interstices of a crystal lattice of the dicalcium silicate.

The tricalcium aluminate in which the silicon atom is solid-soluted may be obtained through substitution of a portion of an aluminum atom of the tricalcium aluminate with the silicon atom, or through entry of the silicon atom into interstices of a crystal lattice of the tricalcium aluminate.

The tricalcium aluminate in which the silicon atom is solid-soluted may include 0.1 to 5 wt % of silicon (Si) that is solid-soluted.

The tricalcium silicate in which the aluminum atom is solid-soluted or the dicalcium silicate in which the aluminum atom is solid-soluted may include 0.1 to 5 wt % of aluminum that is solid-soluted.

The root-canal sealer composition may further include at least one selected from among a radiopaque material, a calcium phosphate compound, and a curing modifier.

The root-canal sealer composition may include 100 parts by weight of the cement, 10 to 100 parts by weight of the hygroscopic liquid, and at least one of 20 to 200 parts by weight of the radiopaque material, 1 to 50 parts by weight of the calcium phosphate compound, and 0.1 to 20 parts by weight of the curing modifier.

In the cement, the ratio of the sum of weights of the tricalcium silicate in which the aluminum atom is solid-soluted (Al solid-soluted C3S) and the dicalcium silicate in which the aluminum atom is solid-soluted (Al solid-soluted C2S) (Al solid-soluted C3S+Al solid-soluted C2S, C) and the weight of the tricalcium aluminate in which the silicon atom is solid-soluted (Si solid-soluted C3A, A) (C:A) may be 99:1 to 70:30.

The cement may be a material prepared by allowing a mixture including calcium oxide, silicon dioxide, and aluminum oxide to react through heat treatment, followed by rapid cooling.

The hygroscopic liquid may include polypropylene glycol.

The hygroscopic liquid may include polypropylene glycol, and may further include at least one selected from among ethanol, propanol, vegetable oil, animal oil, ethylene glycol, propylene glycol, polyethylene glycol, and glycerin.

The calcium phosphate compound may include at least one selected from among calcium phosphate, dicalcium phosphate, tricalcium phosphate, tetracalcium phosphate, hydroxyapatite, apatite, octacalcium phosphate, biphasic calcium phosphate, amorphous calcium phosphate, casein phosphopeptide-amorphous calcium phosphate, and bioactive glass.

The radiopaque material may include at least one selected from among zinc oxide, barium sulfate, zirconium oxide, bismuth oxide, barium oxide, iodoform, tantalum oxide, and calcium tungstate.

The curing modifier may include at least one selected from among calcium sulfate dihydrate, calcium sulfate hemihydrate, calcium chloride, and calcium formate.

Another aspect of the present disclosure provides a method of preparing a root-canal sealer composition including (a) preparing cement and (b) preparing a composition including the cement and a hygroscopic liquid, in which the cement includes tricalcium silicate ($3CaO \cdot SiO_2$) in which an aluminum atom (Al) is solid-soluted (Al solid-soluted C3S), dicalcium silicate ($2CaO \cdot SiO_2$) in which an aluminum atom (Al) is solid-soluted (Al solid-soluted C2S), and tricalcium aluminate ($3CaO \cdot Al_2O_3$) in which a silicon atom (Si) is solid-soluted (Si solid-soluted C3A), the tricalcium aluminate being disposed between at least one selected from the group consisting of the tricalcium silicate in which the aluminum atom is solid-soluted (Al solid-soluted C3S) and the dicalcium silicate in which the aluminum atom is solid-soluted (Al solid-soluted C2S).

Here, step (a) may include (a-1) firing a mixture including calcium oxide, silicon dioxide, and aluminum oxide and (a-2) rapidly cooling the fired mixture.

In step (a-2), the rapidly cooling may be performed at a cooling rate of 100° C./min to 200° C./min.

Advantageous Effects

According to the present disclosure, when cement including aluminum solid-soluted tricalcium silicate, aluminum solid-soluted dicalcium silicate, and silicon solid-soluted tricalcium aluminate is prepared and used for a root-canal sealer composition, a curing time is reduced and compressive strength is increased.

In addition, the root-canal sealer composition of the present disclosure is effective at ensuring a sufficient working time, thereby improving workability and storage stability.

BEST MODE

Figure 1:
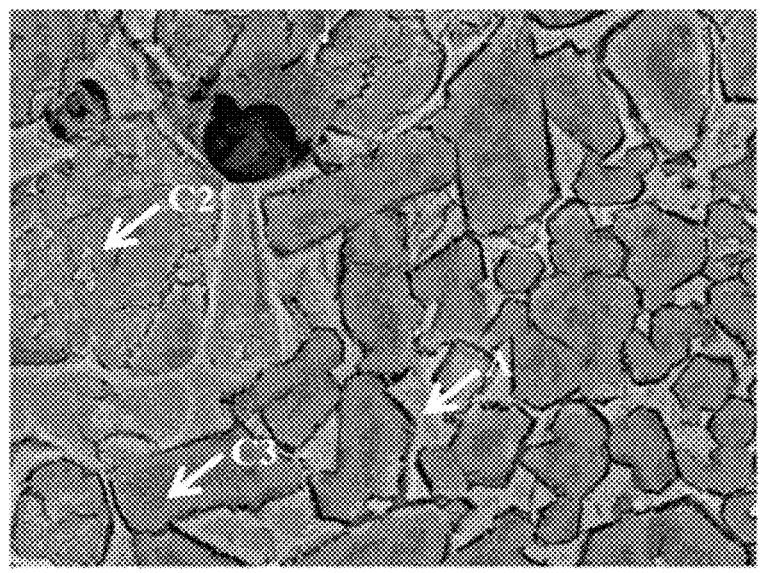
FIG. 1 is a SEM image of the cement prepared according to Preparation Example 2 of the present disclosure.

Hereinafter, exemplary embodiments of the present disclosure are described in detail with reference to the appended drawings so as to be easily performed by a person having ordinary skill in the art.

However, the following description does not limit the present disclosure to specific embodiments, and moreover, descriptions of known techniques, even if they are pertinent to the present disclosure, are considered unnecessary and may be omitted insofar as they would make the characteristics of the disclosure unclear.

The terms herein are used to explain specific embodiments, and are not intended to limit the present disclosure. Unless otherwise stated, a singular expression includes a plural expression. In this application, the terms "comprise", "include" or "have" are used to designate the presence of features, numbers, steps, operations, elements, or combinations thereof described in the specification, and should be understood as not excluding the presence or additional possible presence of one or more different features, numbers, steps, operations, elements, or combinations thereof.

Hereinafter, a detailed description will be given of a root-canal sealer composition of the present disclosure.

The present disclosure pertains to a root-canal sealer composition including cement and a hygroscopic liquid, in which the cement includes tricalcium silicate ($3CaO \cdot SiO_2$) in which an aluminum atom is solid-soluted (Al solid-soluted C3S), dicalcium silicate ($2CaO \cdot SiO_2$) in which an aluminum atom is solid-soluted (Al solid-soluted C2S), and tricalcium aluminate ($3CaO \cdot Al_2O_3$) in which a silicon atom (Si) is solid-soluted (Si solid-soluted C3A), the tricalcium aluminate being disposed between at least one selected from the group consisting of the tricalcium silicate in which the aluminum atom is solid-soluted (Al solid-soluted C3S) and the dicalcium silicate in which the aluminum atom is solid-soluted (Al solid-soluted C2S).

Here, "solid solution" or "solid-soluted" means that an atom of a different element is mixed and distributed in a crystal structure without destroying the original crystal structure, resulting in the same state as a solid-phase solution. It is classified into interstition, in which the atom of a different element is inserted in the gap between atoms, and substitution, in which the atom of a different element pushes out solid atoms that are arranged in an orderly manner and enters in place thereof.

The tricalcium silicate in which the aluminum atom is solid-soluted may be obtained through substitution of a portion of a silicon atom of the tricalcium silicate with the aluminum atom, or through entry of the aluminum atom into interstices of the crystal lattice of the tricalcium silicate.

The dicalcium silicate in which the aluminum atom is solid-soluted may be obtained through substitution of a portion of a silicon atom of the dicalcium silicate with the aluminum atom, or through entry of the aluminum atom into interstices of the crystal lattice of the dicalcium silicate.

The tricalcium aluminate in which the silicon atom is solid-soluted may be obtained through substitution of a portion of an aluminum atom of the tricalcium aluminate with the silicon atom, or through entry of the silicon atom into interstices of the crystal lattice of the tricalcium aluminate.

In the tricalcium aluminate in which the silicon atom is solid-soluted, the silicon (Si) may be solid-soluted in an amount of 0.1 to 5 wt %, preferably 0.1 to 4.0 wt %, and more preferably 0.1 to 2 wt %.

In the tricalcium silicate in which the aluminum atom is solid-soluted or the dicalcium silicate in which the aluminum atom is solid-soluted, the aluminum may be solid-soluted in an amount of 0.10 to 5 wt %, preferably 0.1 to 4.0 wt %, and more preferably 0.1 to 2 wt %.

The root-canal sealer composition may further include a radiopaque material, a calcium phosphate compound, a curing modifier, and the like.

The root-canal sealer composition may include 100 parts by weight of the cement, 10 to 100 parts by weight of the hygroscopic liquid, and at least one of 20 to 200 parts by weight of the radiopaque material, 1 to 50 parts by weight of the calcium phosphate compound, and 0.1 to 20 parts by weight of the curing modifier.

In the cement, the ratio of the sum of the weights of the tricalcium silicate in which the aluminum atom is solid-soluted (Al solid-soluted C3S) and the dicalcium silicate in which the aluminum atom is solid-soluted (Al solid-soluted C2S) (Al solid-soluted C3S+Al solid-soluted C2S, C) and the weight of the tricalcium aluminate in which the silicon atom is solid-soluted (Si solid-soluted C3A, A) (C:A) may be 99:1 to 70:30.

The cement may be a material prepared by allowing a mixture including calcium oxide, silicon dioxide, and aluminum oxide to react through heat treatment, followed by rapid cooling.

The heat treatment may include firing, and the rapid cooling may be performed at a cooling rate of 100° C./min or more from a firing temperature.

The hygroscopic liquid has hygroscopicity and may include polypropylene glycol, and preferably, the hygroscopic liquid includes polypropylene glycol, and further includes ethanol, propanol, vegetable oil, animal oil, ethylene glycol, propylene glycol, polyethylene glycol, glycerin and the like.

Examples of the calcium phosphate compound may include calcium phosphate, dicalcium phosphate, tricalcium phosphate, tetracalcium phosphate, hydroxyapatite, apatite, octacalcium phosphate, biphasic calcium phosphate, amorphous calcium phosphate, casein phosphopeptide-amorphous calcium phosphate, bioactive glass, and the like.

Examples of the radiopaque material may include zinc oxide, barium sulfate, zirconium oxide, bismuth oxide, barium oxide, iodoform, tantalum oxide, calcium tungstate, and the like.

Examples of the curing modifier may include calcium sulfate dihydrate, calcium sulfate hemihydrate, calcium chloride, calcium formate, and the like.

In addition, the present disclosure pertains to a method of preparing the root-canal sealer composition, which is described below.

First, cement is prepared (step a).

The cement may be prepared by allowing a mixture including calcium oxide, silicon dioxide, and aluminum oxide to react through heat treatment, followed by rapid cooling.

Specifically, step (a) may be performed in two steps.

First, a mixture including calcium oxide, silicon dioxide, and aluminum oxide is fired (step a-1).

The firing temperature of the cement configured to include tricalcium silicate in which the aluminum atom is solid-soluted (Al solid-soluted C3S), dicalcium silicate in which the aluminum atom is solid-soluted (Al solid-soluted C2S), and tricalcium aluminate in which the silicon atom is solid-soluted (Si solid-soluted C3A) may be 1200° C. to 1550° C., preferably 1300° C. to 1500° C., and more preferably 1400° C. to 1500° C. Here, if the firing temperature is lower than 1200° C., dicalcium silicate rather than tricalcium silicate may be mainly formed, resulting in reduced cement strength, which is undesirable. On the other hand, if the firing temperature is higher than 1550° C., tricalcium silicate may be formed, but dicalcium silicate and tricalcium silicate, among the components of cement, may decompose during firing, resulting in reduced cement strength, which is undesirable.

The rate of heating to the firing temperature of the cement configured to include tricalcium silicate in which the aluminum atom is solid-soluted (Al solid-soluted C3S), dicalcium silicate in which the aluminum atom is solid-soluted (Al solid-soluted C2S), and tricalcium aluminate in which the silicon atom is solid-soluted (Si solid-soluted C3A) may be 1° C./min to 20° C./min, and preferably 2° C./min to 10° C./min. If the rate of heating to the firing temperature is less than 1° C./min, productivity may decrease due to the excessively long processing time, which is undesirable. On the other hand, if the heating rate exceeds 20° C./min, the time required to react the mixed materials may not be sufficient, and thus some of the materials may remain unchanged, resulting in reduced cement strength, which is undesirable.

The firing time in the temperature range for forming the cement configured to include tricalcium silicate in which the aluminum atom is solid-soluted (Al solid-soluted C3S), dicalcium silicate in which the aluminum atom is solid-soluted (Al solid-soluted C2S), and tricalcium aluminate in which the silicon atom is solid-soluted (Si solid-soluted C3A) may be 0.5 to 24 hours, and preferably 1 to 12 hours.

If the firing time is less than 0.5 hours, the reaction time between the mixed materials may not be sufficient, and thus some of the calcium oxide, silicon dioxide and aluminum oxide may remain unchanged, resulting in reduced cement strength, which is undesirable. On the other hand, if the firing time exceeds 24 hours, economic benefits may be negated due to excessive energy consumption.

Thereafter, the fired mixture is rapidly cooled (step a-2).

The rapid cooling may be performed at a cooling rate of 100° C./min to 200° C./min.

The rapid cooling is specifically described in detail. The cement configured to include tricalcium silicate in which the aluminum atom is solid-soluted (Al solid-soluted C3S), dicalcium silicate in which the aluminum atom is solid-soluted (Al solid-soluted C2S), and tricalcium aluminate in which the silicon atom is solid-soluted (Si solid-soluted C3A) is preferably subjected to rapid cooling so that the structure of Al solid-soluted C3S or Al solid-soluted C2S and Si solid-soluted C3A at the firing temperature is maintained at room temperature. To this end, it is preferable that the rapid cooling in the step of preparing the cement be performed at a cooling rate of 100° C./min or more from the firing temperature. If the cooling rate is less than 100° C./min, the state in which the aluminum atom or the silicon atom is solid-soluted in the lattice structure may not be maintained, but aluminum oxide or silicon dioxide may be formed, resulting in reduced cement strength.

The cement may include tricalcium silicate ($3CaO \cdot SiO_2$) in which the aluminum atom is solid-soluted (Al solid-soluted C3S), dicalcium silicate ($2CaO \cdot SiO_2$) in which the aluminum atom is solid-soluted (Al solid-soluted C2S), and tricalcium aluminate ($3CaO \cdot Al_2O_3$) in which the silicon atom (Si) is solid-soluted (Si solid-soluted C3A), the tricalcium aluminate being disposed between at least one selected from the group consisting of the tricalcium silicate in which the aluminum atom is solid-soluted (Al solid-soluted C3S) and the dicalcium silicate in which the aluminum atom is solid-soluted (Al solid-soluted C2S).

Finally, a composition including the cement and a hygroscopic liquid is prepared (step b).

In step (b), a radiopaque material, a calcium phosphate compound, and a curing modifier may be further added and mixed therein, thereby yielding a composition.

Mode for Disclosure

EXAMPLES

A better understanding of the present disclosure may be obtained through the following examples. However, these examples are merely set forth to illustrate the present disclosure, and are not to be construed as limiting the scope of the present disclosure.

Preparation Example 1: Synthetic Portland Cement (Ordinary Portland Cement, OPC)

72.0 wt % of calcium oxide, 26.3 wt % of silicon dioxide, 1.0 wt % of aluminum oxide, 0.4 wt % of iron oxide, and 0.3 wt % of magnesium oxide were allowed to stand at 100° C. for 24 hours or more before mixing, thereby evaporating water therefrom. In order to uniformly mix and pulverize the materials, ceramic balls having sizes of 10 mm, 5 mm and 1 mm were placed in a V-type mixer in the same volume as the volume of the materials, followed by mixing at 50 rpm for 4 hours.

After mixing, the ceramic balls were removed and the materials were prepared into a tube-shaped green compact in order to make the reaction uniform throughout the materials, after which the compact was placed in a platinum crucible and fired at 1,500° C. for 1 hour 30 minutes. After firing, the sample was immediately recovered and rapidly cooled to 25° C. at a rate of 150° C./min using a cooling fan in ambient air. The fired cement was subjected to primary dry pulverization, after which the primarily pulverized cement was pulverized for 24 hours using ceramic balls having sizes of 10 mm, 5 mm and 1 mm. The materials thus pulverized were sieved, thereby obtaining a cement powder having an average particle size of 10 vm.

The cement powder thus obtained was subjected to XRD analysis under conditions of a CuKα1 wavelength (1.54056 Å), 2p of 25-50° and a scan speed of 5°/min.

Preparation Example 2: Preparation of Cement Including Aluminum Solid-Soluted Tricalcium Silicate, Aluminum Solid-Soluted Dicalcium Silicate, and Silicon Solid-Soluted Tricalcium Aluminate The cement of Preparation Example 2 was prepared in the same manner as in Preparation Example 1, with the exception that 70.8 wt % of calcium oxide, 25.2 wt % of silicon dioxide, and 4.0 wt % of aluminum oxide were used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1. The cement powder of Preparation Example 2 was also analyzed in the same manner as in Preparation Example 1.

Preparation Example 3: Cement in which Aluminum and Silicon Atoms are Excessively Solid-Soluted Cement was prepared in the same manner as in Preparation Example 1, with the exception that a powder including 65.0 wt % of calcium oxide, 27.7 wt % of silicon dioxide, and 7.3 wt % of aluminum oxide was used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1. The cement powder of Preparation Example 3 was also analyzed in the same manner as in Preparation Example 1.

Preparation Example 4: Cement in which Silicon Atom is Solid-Soluted

Cement was prepared in the same manner as in Preparation Example 1, with the exception that a powder including 70.5 wt % of calcium oxide, 22.5 wt % of silicon dioxide, and 7.0 wt % of aluminum oxide was used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1. The cement powder of Preparation Example 4 was also analyzed in the same manner as in Preparation Example 1.

Comparative Preparation Example 1: Cement Including Silicon Dioxide

Cement was prepared in the same manner as in Preparation Example 1, with the exception that a powder including 73.7 wt % of calcium oxide and 26.3 wt % of silicon dioxide was used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1. The cement powder of Comparative Preparation Example 1 was also analyzed in the same manner as in Preparation Example 1.

Comparative Preparation Example 2: Cement Excluding Calcium Aluminate

Cement was prepared in the same manner as in Preparation Example 1, with the exception that a powder including 70.8 wt % of calcium oxide and 29.2 wt % of silicon dioxide was used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1, and air cooling at a rate of 25° C./min was performed, rather than rapid cooling, after firing at 1500° C. The cement powder of Comparative Preparation Example 2 was also analyzed in the same manner as in Preparation Example 1.

Comparative Preparation Example 3: Cement Including Silicon Dioxide

Cement was prepared in the same manner as in Preparation Example 1, with the exception that a powder including 67.5 wt % of calcium oxide, 25.5 wt % of silicon dioxide, 4.5 wt % of aluminum oxide and 2.5 wt % of iron oxide was used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1, and air cooling at a rate of 25° C./min was performed, rather than rapid cooling, after firing at 1500° C. The cement powder of Comparative Preparation Example 3 was also analyzed in the same manner as in Preparation Example 1.

Comparative Preparation Example 4: Cement

Cement was prepared in the same manner as in Preparation Example 1, with the exception that 70.8 wt % of calcium oxide, 25.2 wt % of silicon dioxide and 4.0 wt % of aluminum oxide were used, rather than using 72.0 wt % of calcium oxide, 26.3 wt % of silicon dioxide, 1.0 wt % of aluminum oxide, 0.4 wt % of iron oxide, and 0.3 wt % of magnesium oxide as in Preparation Example 1, and air cooling at a rate of 25° C./min was performed, rather than rapid cooling, after firing at 1500° C. The cement powder of Comparative Preparation Example 4 was also analyzed in the same manner as in Preparation Example 1.

The components, amounts, firing temperature, and cooling process of the cement prepared according to Preparation Examples 1 to 4 and Comparative Preparation Examples 1 to 4 are summarized in Table 1 below.

TABLE 1

| Classification | Calcium oxide (wt %) | Silicon dioxide (wt %) | Aluminum oxide (wt %) | Iron oxide (wt %) | Magnesium oxide (wt %) | Firing temperature (° C.) | Cooling process (cooling rate) |
|---|---|---|---|---|---|---|---|
| Preparation Example 1 | 72.0 | 26.3 | 1.0 | 0.4 | 0.3 | 1,500 | Rapid cooling (150° C./min) |
| Preparation Example 2 | 70.8 | 25.2 | 4.0 | — | — | 1,500 | Rapid cooling (150° C./min) |
| Preparation Example 3 | 65.0 | 27.7 | 7.3 | — | — | 1,500 | Rapid cooling (150° C./min) |
| Preparation Example 4 | 70.5 | 22.5 | 7.0 | — | — | 1,500 | Rapid cooling (150° C./min) |
| Comparative Preparation Example 1 | 73.7 | 26.3 | — | — | — | 1,500 | Rapid cooling (150° C./min) |
| Comparative Preparation Example 2 | 70.8 | 29.2 | — | — | — | 1,500 | Air cooling (25° C./min) |
| Comparative Preparation Example 3 | 67.5 | 25.5 | 4.5 | 2.5 | — | 1,500 | Air cooling (25° C./min) |
| Comparative Preparation Example 4 | 70.8 | 25.2 | 4.0 | — | — | 1,500 | Air cooling (25° C./min) |

Example 1: Preparation of Root-Canal Sealer Composition Including Cement of Preparation Example 2

50 wt % of the cement prepared according to Preparation Example 2, 20 wt % of polypropylene glycol (Mn: 425 g/mol, water content: <0.05 wt %), 27 wt % of zirconium oxide, and 3 wt % of calcium sulfate dihydrate were prepared such that the total mass thereof was 100 g, mixed at 100 rpm for 4 hours, and maintained for 30 minutes in a vacuum (−0.095±0.005 MPa) in order to remove air bubbles formed inside the composition and increase the filling density.

Thereafter, the composition was placed in a container, thereby yielding a root-canal sealer composition.

Example 2: Root-Canal Sealer Composition Including Cement of Preparation Example 3

A root-canal sealer composition was prepared in the same manner as in Example 1, with the exception that the cement prepared according to Preparation Example 3 was used, in lieu of the cement prepared according to Preparation Example 2.

Example 3: Preparation of Root-Canal Sealer Composition Including Cement of Preparation Example 4

A root-canal sealer composition was prepared in the same manner as in Example 1, with the exception that the cement prepared according to Preparation Example 4 was used, in lieu of the cement prepared according to Preparation Example 2.

Example 4: Preparation of Root-Canal Sealer Composition

A root-canal sealer composition was prepared in the same manner as in Example 1, with the exception that 60 wt % of the cement prepared according to Preparation Example 2 and 10 wt % of polypropylene glycol were used, in lieu of 50 wt % of the cement prepared according to Preparation Example 2 and 20 wt % of polypropylene glycol.

Example 5: Preparation of Root-Canal Sealer Composition

A root-canal sealer composition was prepared in the same manner as in Example 1, with the exception that 48 wt % of the cement prepared according to Preparation Example 2 and 2 wt % of bioactive glass $((SiO_2)_9(Na_2O)_5(CaO)_5(P_2O_5)_1)$ were used, in lieu of 50 wt % of the cement prepared according to Preparation Example 2.

Example 6: Preparation of Root-Canal Sealer Composition

A root-canal sealer composition was prepared in the same manner as in Example 1, with the exception that 48 wt % of the cement prepared according to Preparation Example 2 and 2 wt % of tricalcium phosphate were used, in lieu of 50 wt % of the cement prepared according to Preparation Example 2.

Comparative Example 1: Root-Canal Sealer Composition Including Cement of Preparation Example 1

A root-canal sealer composition was prepared in the same manner as in Example 1, with the exception that the cement prepared according to Preparation Example 1 was used, in lieu of the cement prepared according to Preparation Example 2.

Comparative Example 2: Root-Canal Sealer Composition Including Cement of Comparative Preparation Example 2

A root-canal sealer composition was prepared in the same manner as in Example 1, with the exception that the cement of Comparative Preparation Example 2 was used, in lieu of the cement prepared according to Preparation Example 2.

Comparative Example 3: Preparation of Root-Canal Sealer Composition Including Cement of Comparative Preparation Example 3

A root-canal sealer composition was prepared in the same manner as in Example 1, with the exception that the cement prepared according to Comparative Preparation Example 3 was used, in lieu of the cement prepared according to Preparation Example 2.

Comparative Example 4: Preparation of Root-Canal Sealer Composition Including Cement of Comparative Preparation Example 4

A root-canal sealer composition was prepared in the same manner as in Example 1, with the exception that the cement prepared according to Comparative Preparation Example 4 was used, in lieu of the cement prepared according to Preparation Example 2.

Comparative Example 5: Preparation of Root-Canal Sealer Composition Including Cement of Comparative Preparation Example 1

A root-canal sealer composition was prepared in the same manner as in Example 1, with the exception that the cement prepared according to Comparative Preparation Example 1 was used, in lieu of the cement prepared according to Preparation Example 2.

The components and amounts of the root-canal sealer compositions prepared according to Examples 1 to 6 and Comparative Examples 1 to 5 are shown in Table 2 below.

TABLE 2

| Classification | Cement (wt %) | | Polypropylene glycol (wt %) | Zirconium oxide (wt %) | Calcium sulfate dihydrate (wt %) | Tricalcium phosphate (wt %) | Bioactive glass (wt %) |
|---|---|---|---|---|---|---|---|
| Example 1 | Preparation Example 2 | 50 | 20 | 27 | 3 | — | — |
| Example 2 | Preparation Example 3 | 50 | 20 | 27 | 3 | — | — |
| Example 3 | Preparation Example 4 | 50 | 20 | 27 | 3 | — | — |
| Example 4 | Preparation Example 2 | 60 | 10 | 27 | 3 | — | — |
| Example 5 | Preparation Example 2 | 58 | 20 | 27 | 3 | — | 2 |
| Example 6 | Preparation Example 2 | 58 | 20 | 27 | 3 | 2 | — |

TABLE 2-continued

| Classification | Cement (wt %) | | Polypropylene glycol (wt %) | Zirconium oxide (wt %) | Calcium sulfate dihydrate (wt %) | Tricalcium phosphate (wt %) | Bioactive glass (wt %) |
|---|---|---|---|---|---|---|---|
| Comparative Example 1 | Preparation Example 1 | 50 | 20 | 27 | 3 | — | — |
| Comparative Example 2 | Comparative Preparation Example 2 | 50 | 20 | 27 | 3 | — | — |
| Comparative Example 3 | Comparative Preparation Example 3 | 50 | 20 | 27 | 3 | — | — |
| Comparative Example 4 | Comparative Preparation Example 4 | 50 | 20 | 27 | 3 | — | — |
| Comparative Example 5 | Comparative Preparation Example 1 | 50 | 20 | 27 | 3 | — | — |

TEST EXAMPLES

Test Example 1: Confirmation of Composition of Cement

FIG. 1 shows an SEM image of a cross section of the cement prepared according to Preparation Example 2, and Table 3 below shows the results of EDS analysis thereof. In FIG. 1, aluminum solid-soluted tricalcium silicate (Al solid-soluted C3S), aluminum solid-soluted dicalcium silicate (Al solid-soluted C2S) and silicon solid-soluted tricalcium aluminate (Si solid-soluted C3A) are represented as C3, C2 and A, respectively.

As shown in the cross-section of FIG. 1, the cement prepared according to Preparation Example 2 was configured such that silicon solid-soluted tricalcium aluminate was interposed between euhedral aluminum solid-soluted tricalcium silicate and anhedral aluminum solid-soluted dicalcium silicate.

In addition, in the cross-section of the cement of Preparation Example 2, which was rapidly cooled, a dicalcium silicate (C2S) precipitate phase in tricalcium aluminate (C3A) or a tricalcium aluminate (C3A) precipitate phase in tricalcium silicate (C3S), formed upon air cooling (slow cooling), did not appear. Moreover, a lamella structure, formed while C3A was generally crystallized upon slow cooling of a melt, was not W observed.

In addition, as is apparent from the results of EDS analysis of Table 3 below, the cement prepared according to Preparation Example 2 was composed of Al solid-soluted C3S, Al solid-soluted C2S, and Si solid-soluted C3A. In the case of C3 and C2, it was confirmed that the atomic ratio of calcium, silicon and oxygen stoichiometrically matched that of C3S and C2S, and thus excess aluminum did not form an equilibrium compound but was solid-soluted in the C3S and C2S structures.

TABLE 3

| Classification | Ca (wt %) | Si (wt %) | Al (wt %) | O (wt %) | Total (wt %) |
|---|---|---|---|---|---|
| C3 | 50.02 | 12.21 | 1.83 | 35.94 | 100 |
| C2 | 42.83 | 16.14 | 1.98 | 39.05 | 100 |
| A | 41.18 | 2.39 | 19.78 | 36.65 | 100 |

Test Example 2: XRD Analysis of Cement

FIGS. 2a to 2d show the XRD patterns of Preparation Examples 1 to 4, and FIGS. 2e to 2h show the XRD patterns of Comparative Preparation Examples 1 to 4. FIG. 2i shows the enlarged C3S peak among the XRD patterns of the cement prepared according to Preparation Example 2, Preparation Example 3 and Comparative Preparation Example 2, and FIG. 2j shows the enlarged C3A peak among the XRD patterns of the cement prepared according to Preparation Example 2 and Preparation Example 3.

With reference to FIGS. 2a to 2h, it was confirmed that tricalcium silicate (C3S), dicalcium silicate (C2S) and tricalcium aluminate (C3A) were formed in the cement in all cases other than Comparative Preparation Example 1 and Comparative Preparation Example 2. Since the cement prepared according to Comparative Preparation Example 1 and Comparative Preparation Example 2 did not include aluminum oxide, only C3S and C2S were formed.

Figure 2A:
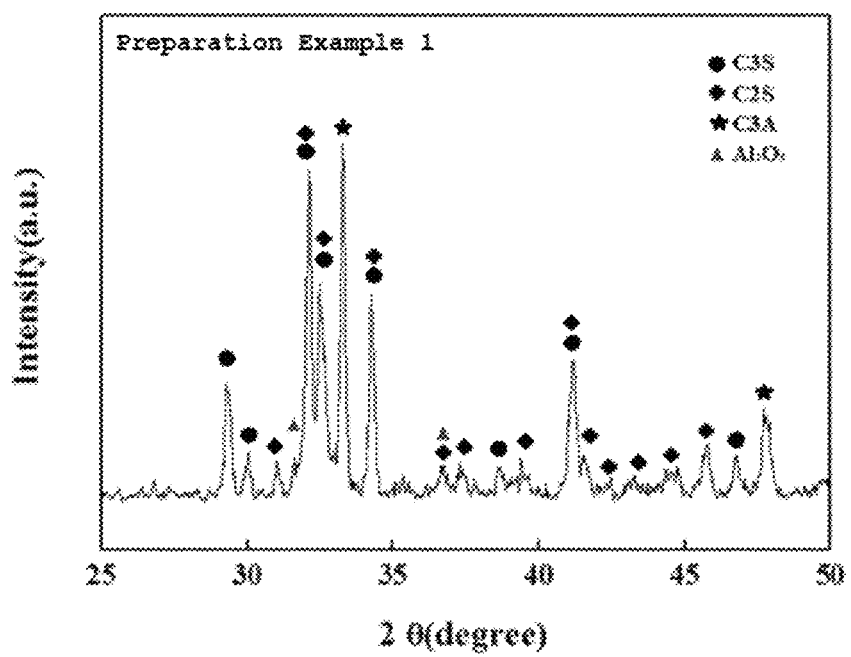
FIG. 2a shows the results of analysis of X-ray diffraction (XRD) of the cement prepared according to Preparation Example 1.
Figure 2B:
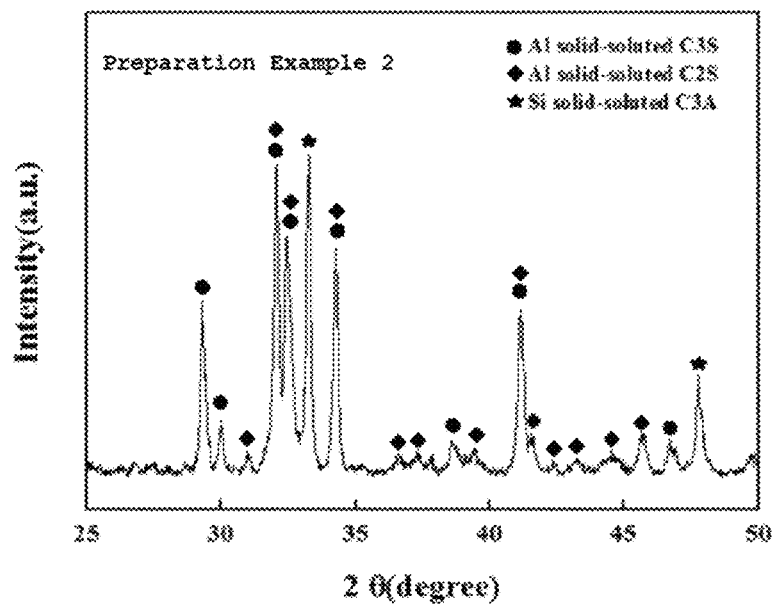
FIG. 2b shows the results of analysis of X-ray diffraction (XRD) of the cement prepared according to Preparation Example 2.
Figure 2C:
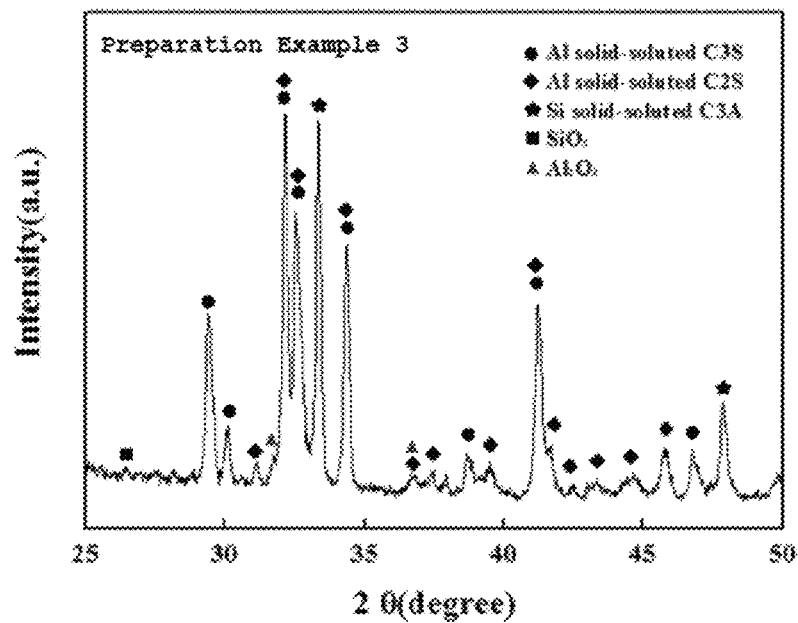
FIG. 2c shows the results of analysis of X-ray diffraction (XRD) of the cement prepared according to Preparation Example 3.
Figure 2D:
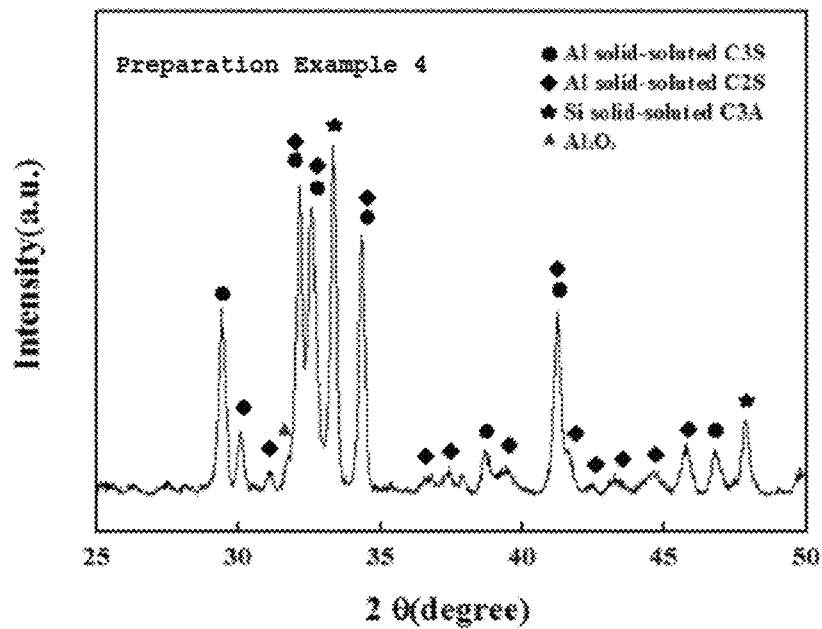
FIG. 2d shows the results of analysis of X-ray diffraction (XRD) of the cement prepared according to Preparation Example 4.
Figure 2E:
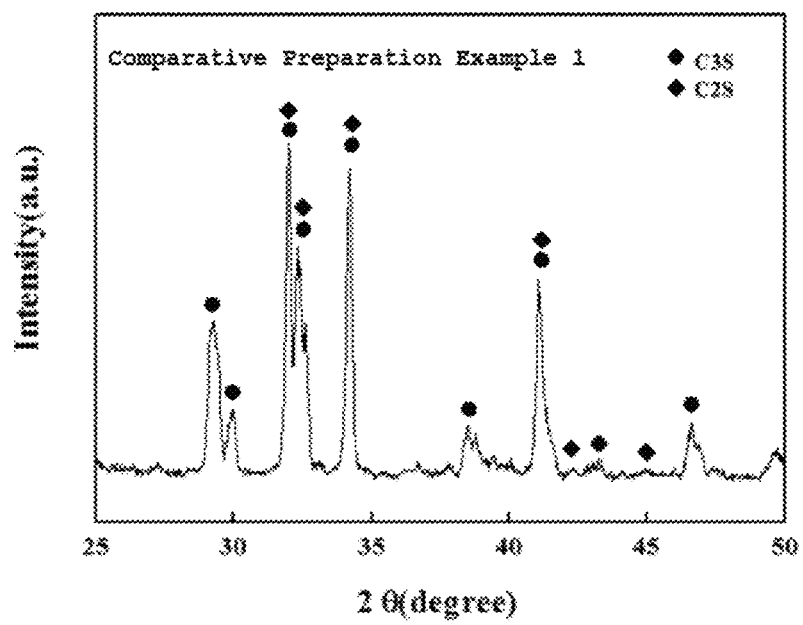
FIG. 2e shows the results of analysis of X-ray diffraction (XRD) of the cement prepared according to Comparative Preparation Example 1.
Figure 2F:
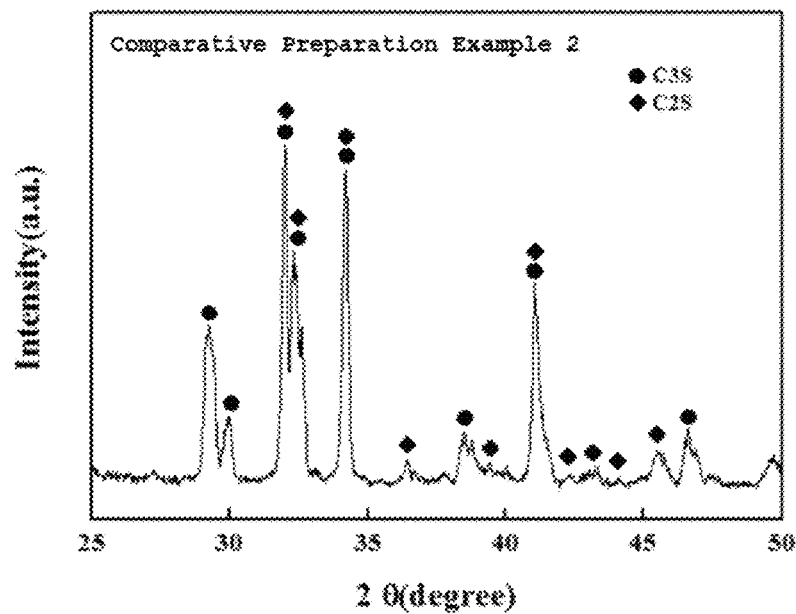
FIG. 2f shows the results of analysis of X-ray diffraction (XRD) of the cement prepared according to Comparative Preparation Example 2.
Figure 2G:
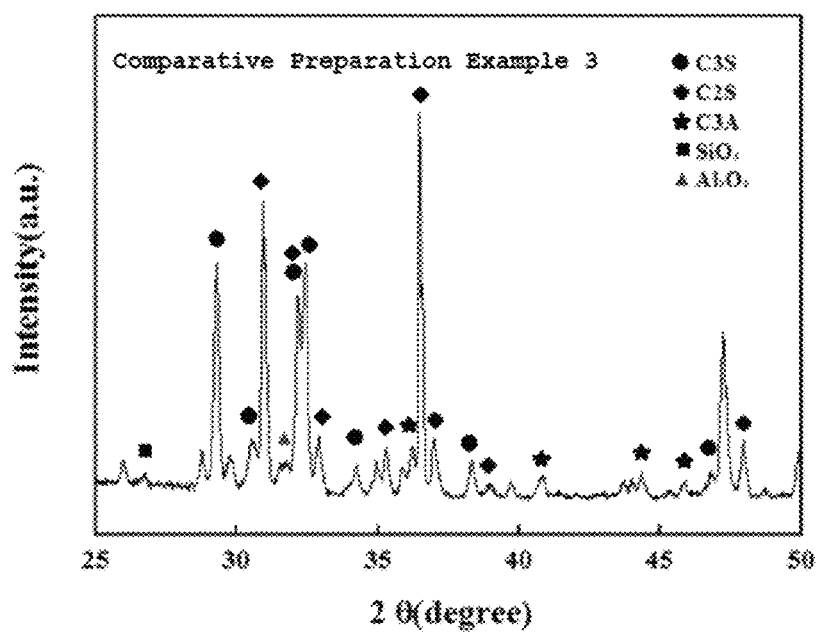
FIG. 2g shows the results of analysis of X-ray diffraction (XRD) of the cement prepared according to Comparative Preparation Example 3.
Figure 2H:
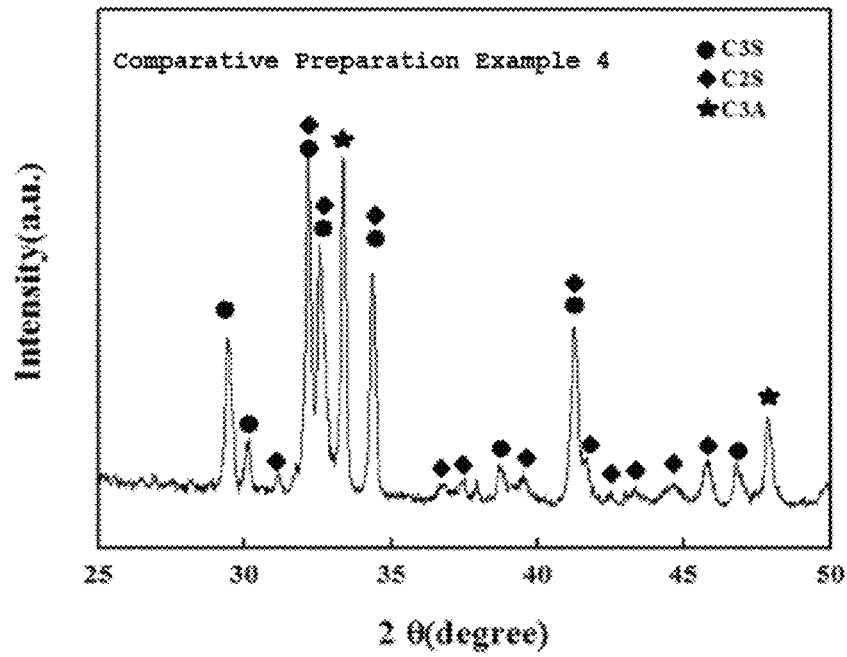
FIG. 2h shows the results of analysis of X-ray diffraction (XRD) of the cement prepared according to Comparative Preparation Example 4.
Figure 2I:
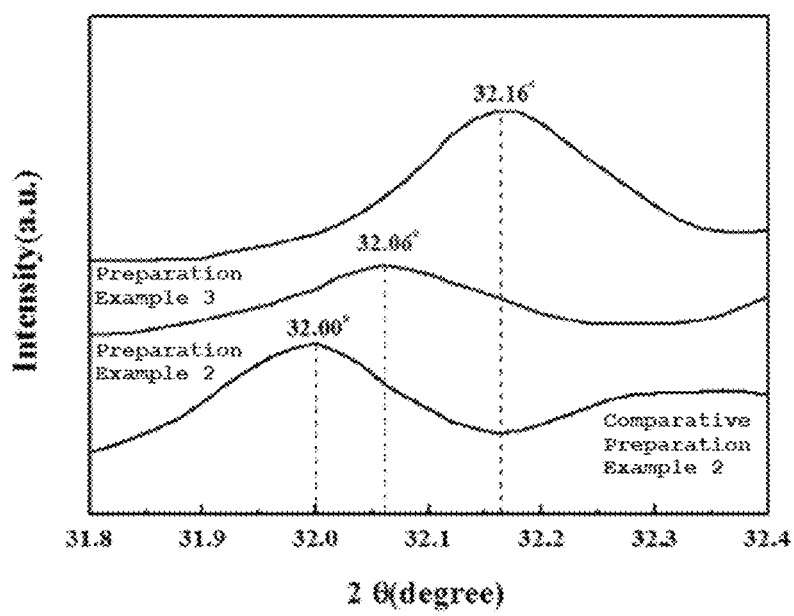
FIG. 2i shows the main peak of C3S among the XRD patterns of the cement prepared according to Preparation Example 2, Preparation Example 3, and Comparative Preparation Example 2.
Figure 2J:
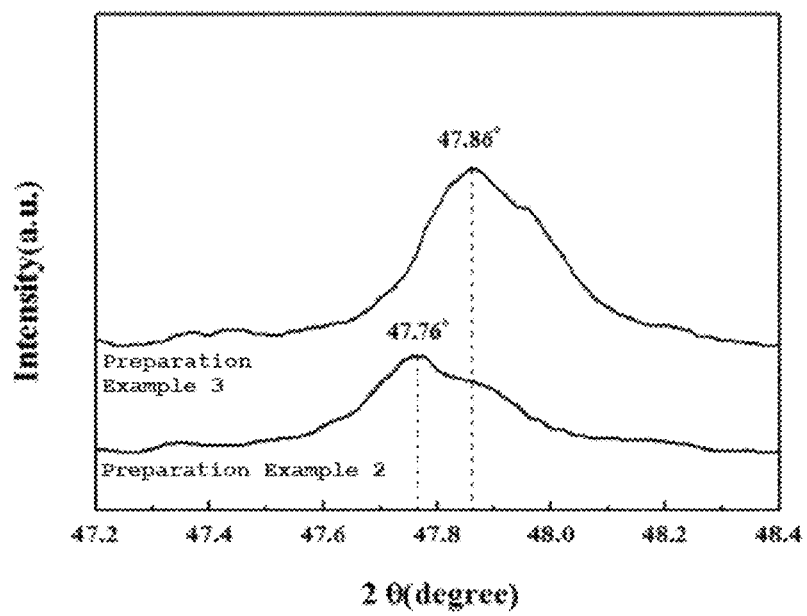
FIG. 2j shows the peak of C3A among the XRD patterns of the cement prepared according to Preparation Example 2 and Preparation Example 3.

With reference to FIGS. 2b and 2c, based on the results of XRD analysis of Preparation Example 3, in which silicon dioxide and aluminum oxide were used in increased amounts compared to Preparation Example 2, upon preparation of cement using the same method, peaks corresponding to the plane (101) of silicon dioxide and the planes (311) and (220) of aluminum oxide were observed. Accordingly, if excess silicon dioxide or aluminum oxide not participating in the formation of C3S, C2S and C3A during the preparation of cement is present, each crystal structure has to appear on the XRD pattern. However, in the XRD pattern of the cement prepared according to Preparation Example 2, it was confirmed that the peaks of silicon dioxide and aluminum oxide did not appear.

This is deemed to be because the above components were completely consumed in the formation of C3S, C2S, and C3A, or decomposed in the firing process, so aluminum oxide was solid-soluted in the lattice of tricalcium silicate and dicalcium silicate, thus forming aluminum solid-soluted tricalcium silicate (Al solid-soluted C3S) and aluminum solid-soluted dicalcium silicate (Al solid-soluted C2S), and also because the silicon atom of silicon dioxide was substituted to the aluminum site of the tricalcium aluminate matrix having a similar atomic size, and was thus distributed in the matrix to form silicon solid-soluted tricalcium aluminate.

In addition, with reference to FIG. 2i, in Comparative Preparation Example 2, the cement was fired using only calcium oxide and silicon dioxide, excluding aluminum oxide, and after firing, slow air cooling was performed, so C3S and C2S could be sufficiently formed. On the other hand, since the cement of Preparation Example 2 and Preparation Example 3 was rapidly cooled after firing, the driving force to form the complete crystal structure of C3A was not maintained, so the main peak of C3S of Comparative Preparation Example 2 did not match that of Preparation Example 2 and Preparation Example 3, which were rapidly cooled.

Thereby, the C3S lattice deformation in the cement of Preparation Example 2 and Preparation Example 3 was confirmed, and the lattice deformation increased with an increase in the amount of aluminum oxide that was added, indicating that aluminum solid-soluted tricalcium silicate in which the aluminum atom was solid-soluted in the lattice structure of C3S was formed.

With reference to FIG. 2j, when comparing Preparation Example 2 and Preparation Example 3, the position of the main peak of C3A changed with an increase in the amount of silicon dioxide. Briefly, it was confirmed that lattice deformation also occurred in the C3A structure, like the lattice structure deformation of C3S.

Test Example 3: Raman Analysis of Cement

Figure 3:
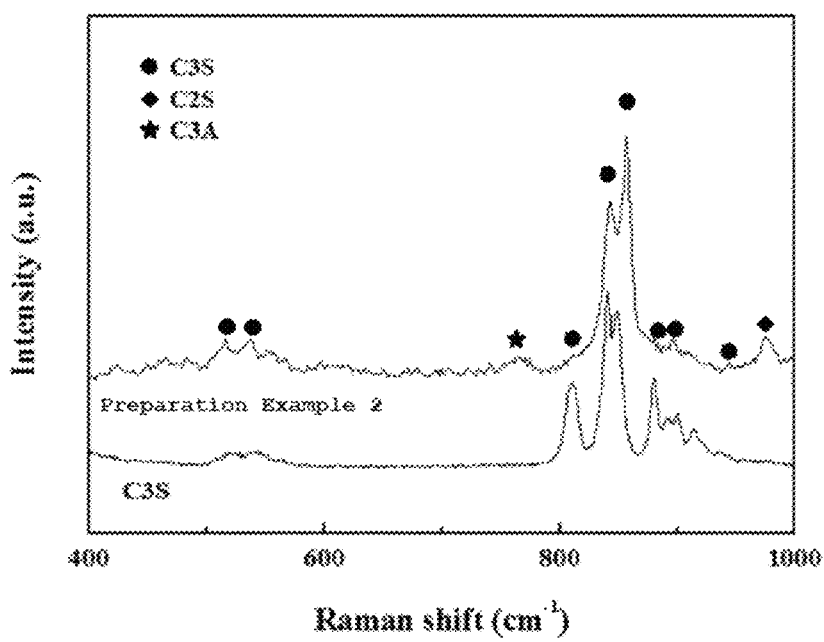
FIG. 3 shows the Raman spectra of C3S and the cement prepared according to Preparation Example 2.

FIG. 3 shows the Raman spectra of the C3S powder and the cement prepared according to Preparation Example 2.

The Raman spectra of the C3S powder, which accounts for the largest amount in the cement, and the cement powder were compared. Based on the results thereof, the peaks of C3S, C2S and C3A were observed, and different frequency changes were confirmed at the peaks of C3S and C2S. There was a great change in the Si—O stretching vibration peak at 800-900 $cm^1$, and particularly, the peak frequency of C3S at 849 $cm^1$ increased to 856 $cm^1$ in the cement, resulting in deformation in which the bond length of Si—O was decreased.

In addition, the peak frequency of the cement at 542 $cm^1$ due to the bending of Si—O decreased to 536 $cm^1$, resulting in deformation in which the bond strength was weakened.

Based on these results, it can be judged that the contraction and expansion of $SiO_2$ molecules present in the structure occur due to the entry of the aluminum atom into interstices of the C3S structure.

Test Example 4: Analysis of Properties of Root-Canal Sealer Composition

The results of analysis of curing time, flowability, and compressive strength of the dental compositions prepared according to Examples 1 to 6 and Comparative Examples 1 to 5 are summarized in Table 4 below.

TABLE 4

| Classification | Curing time (minutes) | Flowability (mm) | Compressive strength (MPa) |
|---|---|---|---|
| Example 1 | 17 | 23.3 | 36.8 ± 6.4 |
| Example 2 | 20 | 23.9 | 30.2 ± 5.9 |
| Example 3 | 18 | 23.1 | 32.3 ± 2.6 |
| Example 4 | 11 | 9.7 | 78.1 ± 9.2 |
| Example 5 | 10 | 8.9 | 95.6 ± 7.3 |
| Example 6 | 19 | 10.1 | 75.4 ± 3.5 |
| Comparative Example 1 | 67 | 22.8 | 16.9 ± 2.2 |
| Comparative Example 2 | 39 | 23.5 | 13.4 ± 3.1 |
| Comparative Example 3 | 51 | 25.7 | 10.8 ± 2.7 |
| Comparative Example 4 | 33 | 21.4 | 20.7 ± 1.3 |
| Comparative Example 5 | 26 | 21.9 | 15.5 ± 1.8 |

Test Example 4-1: Analysis of Curing Time

The curing time of the root-canal sealer was evaluated according to ISO 6876:2012. Before evaluation, a gypsum mold having a groove with a diameter of 10 mm and a depth of 1 mm was stored for 24 hours in an oven at 37±1° C. with a humidity of 95% or more. The composition was placed in the groove and the surface thereof was flattened, after which the curing time was evaluated during storage in an oven at 37±1° C. with a humidity of 95% or more. As such, a Gilmore needle having a weight of 100±5 g and a needle diameter of 2±0.1 mm was used, and was placed on the surface of the sample for 15 seconds to evaluate whether the sample was cured. The storage time without indentation on the surface of the composition was determined to be the curing time, and an average of three measured values was calculated. The results thereof are shown in Table 4.

As shown in Table 4, the root-canal sealer compositions of Examples 1 to 6 exhibited a short curing time compared to Comparative Examples. The root-canal sealer composition prepared according to Comparative Example 2, having high C2S content and not including C3A, can be judged to have a lengthened curing time. In the root-canal sealer composition prepared according to Comparative Example 3, silicon dioxide and aluminum oxide not participating in the hydrocuring of C3S, C2S and C3A were present in the cement, based on which it can be judged that the formation of the C-S-H gel was interrupted. In the cement of Examples 1 to 3, a portion of the aluminum atom that is solid-soluted in tricalcium silicate (C3S) or dicalcium silicate (C2S) is capable of being substituted with silicon of the Dreierketten chain when forming the C-S-H gel, thus increasing the gap of the C-S-H gel and the length of the gel, thereby promoting the curing reaction and increasing compressive strength. However, when comparing Examples 1 and 2, the formation of the C-S-H gel in Example 2 was interrupted by silicon dioxide and aluminum oxide remaining in the cement despite the solid solution of aluminum and silicon atoms, and the curing reaction was slow compared to Example 1.

Test Example 4-2: Analysis of Flowability

For the evaluation of flowability of the root-canal sealer composition, two glass plates having a size of 40 mm×40 mm, a thickness of 5 mm and a weight of 20 g were used according to ISO 6876:2012. 0.05±0.005 ml of the root-canal sealer composition was placed on one glass plate, the sample was covered with another glass plate, and a 100 g weight was placed thereon for 10 minutes. After removing the weight, the maximum and minimum diameters of the root-canal sealer composition between the two glass plates were measured. Here, an average of a total of three measurements obtained by selecting only results in which the variation between the maximum and minimum diameters was 1 mm or less was calculated, and the results thereof are shown in Table 4.

As is apparent from Table 4, since the flowability of the root-canal sealer is affected by the amount of the cement and the amount of the hygroscopic liquid, in Examples 1 to 3 and Comparative Examples 1 to 5, in which the amounts of cement and hygroscopic liquid are the same, there was a great difference in flowability. However, it was confirmed that the flowability of the dental compositions of Examples 4 to 6, in which the amount of the cement was increased, was notably reduced.

Test Example 4-3: Analysis of Compressive Strength

A compressive strength specimen of the root-canal sealer composition was manufactured in a manner in which the sample was placed in a hole 4 mm in diameter and 6 mm in depth of a gypsum mold according to ISO 6876:2012, stored for 7 days in an oven at 37±1° C. with a humidity of 95% or more, and then removed therefrom. The removed specimen was subjected to a compressive strength test at a speed of 1 mm/min using an Instron-type universal testing machine, and an average of five measured values was calculated. The results thereof are shown in Table 4.

As is apparent from Table 4, the results of the compressive strength test showed that the root-canal sealer composition prepared according to the Examples having high cement content exhibited higher compressive strength than the root-canal sealer composition prepared under different conditions.

Test Example 5: Clinical Test for Root-Canal Filling

Figure 4:
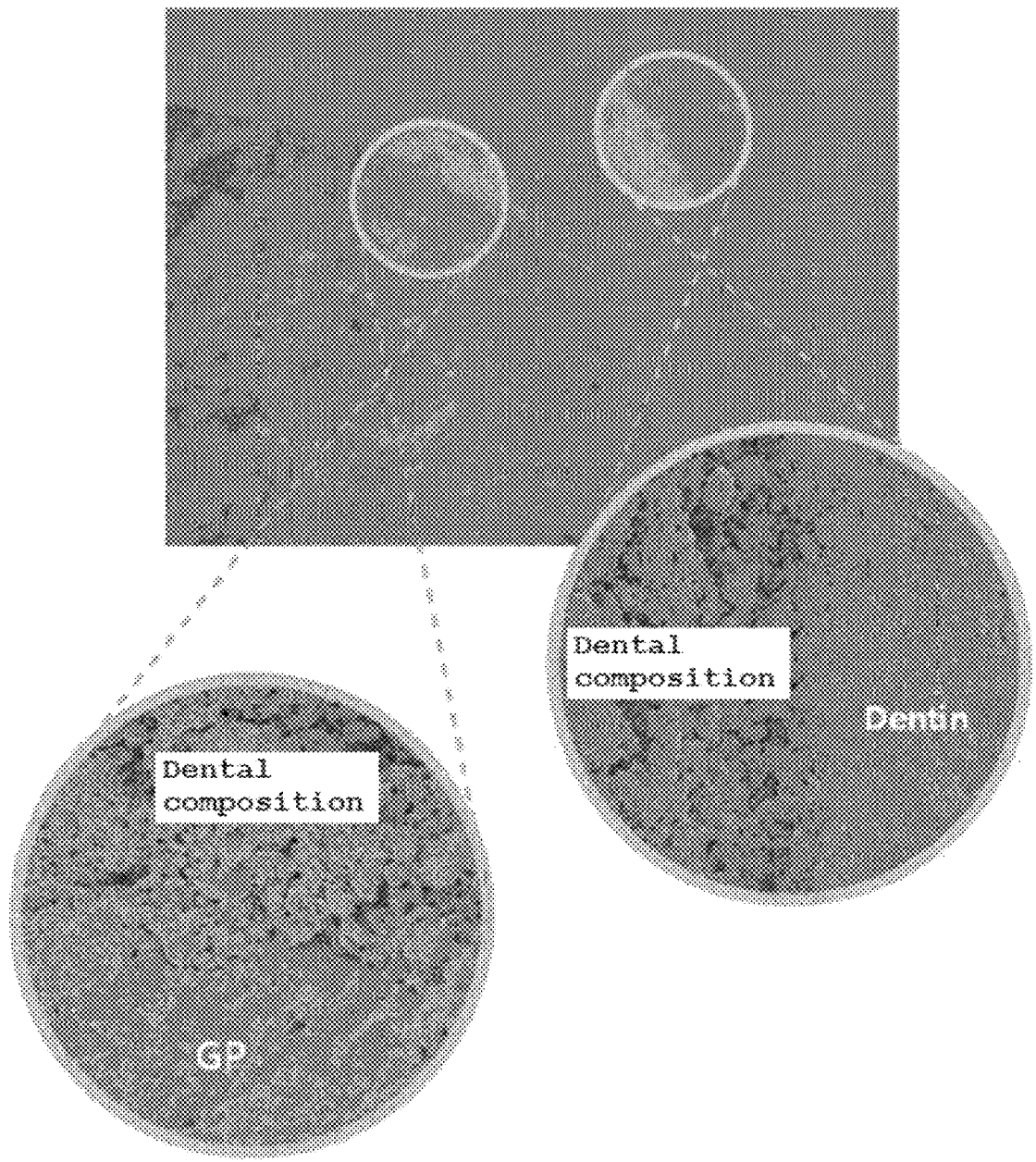
FIG. 4 shows images of observation of the interface between the composition and each of dentin and GP (glycerol phosphate disodium salt) after filling the root canal with the composition prepared according to Example 5.
Figure 5:
FIG. 5 is a radiographic image showing the filled state after filling the root canal with the composition of Example 5 of the present disclosure.

FIG. 4 shows images of observation of the interface between the composition and each of dentin and GP after filling the root canal with the composition of Example 5, and FIG. 5 is a radiographic image showing the filled state after filling the root canal with the composition of Example 5 of the present disclosure.

The root-canal sealer composition prepared according to Example 5 of the present disclosure was placed in a syringe, and a dispensing tip was provided thereto in order to fill the root canal therewith. With reference to FIG. 4, it can be seen that the root-canal sealer composition of Example 5 was densely attached between the dentin layer of the tooth and the gutta-percha to form an interface. If the root-canal sealer composition does not form a strong interface between dentin and gutta-percha, a microleak may develop after the procedure, resulting in increased likelihood of secondary caries.

FIG. 5 is an X-ray image showing the state after filling the root canal with the root-canal sealer composition prepared according to Example 5, indicating that fine portions of the root canal were efficiently filled with the composition.

The scope of the present disclosure is represented by the claims below rather than the aforementioned detailed description, and all changes or modified forms that are capable of being derived from the meaning, range, and equivalent concepts of the appended claims should be construed as being included in the scope of the present disclosure.

INDUSTRIAL APPLICABILITY

According to the present disclosure, when cement including aluminum solid-soluted tricalcium silicate, aluminum solid-soluted dicalcium silicate, and silicon solid-soluted tricalcium aluminate is prepared and used for a root-canal sealer composition, a curing time is reduced and compressive strength is increased.

In addition, the root-canal sealer composition of the present disclosure is effective at ensuring a sufficient working time, thereby improving workability and storage stability.

The invention claimed is:

1. A root-canal sealer composition, comprising:
   cement; and
   a hygroscopic liquid,
   wherein the cement comprises:
   tricalcium silicate ($3CaO \cdot SiO_2$) in which an aluminum atom (Al) is solid-soluted (Al solid-soluted C3S);
   dicalcium silicate ($2CaO \cdot SiO_2$) in which an aluminum atom (Al) is solid-soluted (Al solid-soluted C2S); and
   tricalcium aluminate ($3CaO \cdot Al_2O_3$) in which a silicon atom (Si) is solid-soluted (Si solid-soluted C3A), the tricalcium aluminate being disposed between at least one selected from the group consisting of the tricalcium silicate in which the aluminum atom is solid-soluted (Al solid-soluted C3S) and the dicalcium silicate in which the aluminum atom is solid-soluted (Al solid-soluted C2S).

2. The root-canal sealer composition of claim 1, wherein the tricalcium silicate in which the aluminum atom is solid-soluted is obtained through substitution of a portion of a silicon atom of the tricalcium silicate with the aluminum atom, or through entry of the aluminum atom into interstices of a crystal lattice of the tricalcium silicate.

3. The root-canal sealer composition of claim 1, wherein the dicalcium silicate in which the aluminum atom is solid-soluted is obtained through substitution of a portion of a silicon atom of the dicalcium silicate with the aluminum atom, or through entry of the aluminum atom into interstices of a crystal lattice of the dicalcium silicate.

4. The root-canal sealer composition of claim 1, wherein the tricalcium aluminate in which the silicon atom is solid-soluted is obtained through substitution of a portion of an aluminum atom of the tricalcium aluminate with the silicon atom, or through entry of the silicon atom into interstices of a crystal lattice of the tricalcium aluminate.

5. The root-canal sealer composition of claim 1, wherein the tricalcium aluminate in which the silicon atom is solid-soluted comprises 0.1 to 5 wt % of silicon (Si) that is solid-soluted.

6. The root-canal sealer composition of claim 1, wherein the tricalcium silicate in which the aluminum atom is solid-soluted or the dicalcium silicate in which the aluminum atom is solid-soluted comprises 0.1 to 5 wt % of aluminum that is solid-soluted.

7. The root-canal sealer composition of claim 1, wherein the root-canal sealer composition further comprises at least one selected from among a radiopaque material, a calcium phosphate compound, and a curing modifier.

8. The root-canal sealer composition of claim 7, wherein the root-canal sealer composition comprises:
   100 parts by weight of the cement;
   10 to 100 parts by weight of the hygroscopic liquid; and
   at least one of 20 to 200 parts by weight of the radiopaque material, 1 to 50 parts by weight of the calcium phosphate compound, and 0.1 to 20 parts by weight of the curing modifier.

9. The root-canal sealer composition of claim 1, wherein a ratio of a sum of weights of the tricalcium silicate in which the aluminum atom is solid-soluted (Al solid-soluted C3S) and the dicalcium silicate in which the aluminum atom is solid-soluted (Al solid-soluted C2S) (Al solid-soluted C3S+ Al solid-soluted C2S, C) and a weight of the tricalcium aluminate in which the silicon atom is solid-soluted (Si solid-soluted C3A, A) (C:A) is 99:1 to 70:30.

10. The root-canal sealer composition of claim 1, wherein the cement is a material prepared by allowing a mixture comprising calcium oxide, silicon dioxide, and aluminum oxide to react through heat treatment, followed by rapid cooling.

11. The root-canal sealer composition of claim 1, wherein the hygroscopic liquid comprises polypropylene glycol.

12. The root-canal sealer composition of claim 1, wherein the hygroscopic liquid comprises polypropylene glycol, and further comprises at least one selected from among ethanol, propanol, vegetable oil, animal oil, ethylene glycol, propylene glycol, polyethylene glycol, and glycerin.

13. The root-canal sealer composition of claim 7, wherein the calcium phosphate compound comprises at least one selected from among calcium phosphate, dicalcium phosphate, tricalcium phosphate, tetracalcium phosphate, hydroxyapatite, apatite, octacalcium phosphate, biphasic calcium phosphate, amorphous calcium phosphate, casein phosphopeptide-amorphous calcium phosphate, and bioactive glass.

14. The root-canal sealer composition of claim 7, wherein the radiopaque material comprises at least one selected from among zinc oxide, barium sulfate, zirconium oxide, bismuth oxide, barium oxide, iodoform, tantalum oxide, and calcium tungstate.

15. The root-canal sealer composition of claim 7, wherein the curing modifier comprises at least one selected from among calcium sulfate dihydrate, calcium sulfate hemihydrate, calcium chloride, and calcium formate.

16. A method of preparing a root-canal sealer composition, comprising:
(a) preparing cement; and
(b) preparing a composition comprising the cement and a hygroscopic liquid,
wherein the cement comprises:
tricalcium silicate ($3CaO \cdot SiO_2$) in which an aluminum atom (Al) is solid-soluted (Al solid-soluted C3S);
dicalcium silicate ($2CaO \cdot SiO_2$) in which an aluminum atom (Al) is solid-soluted (Al solid-soluted C2S); and
tricalcium aluminate ($3CaO \cdot Al_2O_3$) in which a silicon atom (Si) is solid-soluted (Si solid-soluted C3A), the tricalcium aluminate being disposed between at least one selected from the group consisting of the tricalcium silicate in which the aluminum atom is solid-soluted (Al solid-soluted C3S) and the dicalcium silicate in which the aluminum atom is solid-soluted (Al solid-soluted C2S),
(a-1) firing a mixture comprising calcium oxide, silicon dioxide, and aluminum oxide; and
(a-2) rapidly cooling the fired mixture.

17. The method of claim 16, wherein, in step (a-2), the rapidly cooling is performed at a cooling rate of 100° C./min to 200° C./min.

* * * * *